United States Patent [19]

Wang et al.

[11] Patent Number: 5,558,752

[45] Date of Patent: Sep. 24, 1996

[54] EXHAUST GAS SENSOR DIAGNOSTIC

[75] Inventors: Da Y. Wang, Lexington, Mass.; Larry M. Oberdier, Royal Oak, Mich.

[73] Assignee: General Motors Corporation, Detroit, Mich.

[21] Appl. No.: 431,200

[22] Filed: Apr. 28, 1995

[51] Int. Cl.⁶ .................................................. G01N 27/26
[52] U.S. Cl. .......................... 204/401; 204/425; 204/427; 204/406; 123/672; 123/690; 205/775
[58] Field of Search ................................ 204/401, 153.1, 204/425, 427, 406; 123/672, 690

[56] References Cited

U.S. PATENT DOCUMENTS

| | | | |
|---|---|---|---|
| 3,514,377 | 5/1970 | Spacil et al. | 204/1 T |
| 3,661,748 | 5/1972 | Blackmer | 204/401 |
| 3,907,657 | 9/1975 | Heijne et al. | 204/1 T |
| 4,224,113 | 9/1980 | Kimura et al. | 204/1 T |
| 4,272,329 | 6/1981 | Hetrick et al. | 204/1 T |
| 4,462,373 | 7/1984 | Kanno | 123/489 |
| 4,487,680 | 12/1984 | Logothetis et al. | 204/426 |
| 4,532,013 | 7/1985 | Dietz et al. | 204/401 |
| 5,310,472 | 5/1994 | Dietz et al. | 204/425 |

*Primary Examiner*—Bruce F. Bell
*Attorney, Agent, or Firm*—Michael J. Bridges

[57] ABSTRACT

A diagnostic apparatus applied to internal combustion engine exhaust gas sensors employing electrochemical polarographic principles indicates sensor operation relative to a current limiting operating region in which a sensor output signal indicates oxygen concentration in the exhaust gas. A sensor drive signal is controllably perturbed and sensor sensitivity monitored by monitoring the sensor response to the perturbation. Current limiting operation may be diagnosed and indicated when the sensor response indicates an insensitivity to the perturbation.

12 Claims, 3 Drawing Sheets

5,558,752

EXHAUST GAS SENSOR DIAGNOSTIC

FIELD OF THE INVENTION

This invention relates to automotive internal combustion engine exhaust gas sensors and, more particularly, to diagnosing operation of an exhaust gas sensor.

BACKGROUND OF THE INVENTION

Electrochemical polarographic principles are employed in known oxygen sensors including an oxygen pump cell and a Nernst cell built, for example, from solid oxide electrolyte materials such as doped zirconia, and linked together through an external electrical circuit. The Nernst cell includes an air reference electrode (or a biased reference electrode) and a sensing electrode and a solid electrolyte therebetween. The pump cell includes a first and second electrode with a solid electrolyte therebetween and a gas chamber with an aperture. The first electrode of the pump cell and the sensing electrode of the Nernst cell are exposed to the gas chamber which receives a representative flow of test gas, such as engine exhaust gas. A controlled electrical potential is applied to the pump cell to pump oxygen into and out of the gas chamber to maintain the electromotive force EMF of the Nernst cell as sensed at the air reference electrode thereof at a desired potential.

To provide for sensing of the oxygen concentration in the test gas, such as by sensing oxygen flux in the gas chamber, the sensor must be maintained in a current limiting range of operation by maintaining the potential applied to the sensor within a predetermined voltage range. The current limiting range of operation is characterized by a sensor output current that is insensitive to variations in the potential applied to the pump cell. In such a range of operation, oxygen flux into or out of the gas chamber is limited by the aperture and sensor output current indicates the maximum flow that can be supported by the concentration in the test gas. If the potential is above the predetermined voltage range, additional oxygen may be stripped from gas species as $H_2O$ and $CO_2$, skewing the relationship between the potential applied to the sensor and sensor output current. If the potential is below the predetermined voltage range, an excess of oxygen is available and sensor output current does not indicate oxygen concentration but rather is a nonlinear function of the potential applied to the sensor.

To ensure accurate oxygen sensing in the current limiting range of operation, conventional electrochemical polarographic sensors must have stable electrocatalytic effects and must retain certain current limiting properties. If the sensor electrodes lose a portion of their electrocatalytic effect or if the current limiting means of the sensor is damaged, the linear relationship between oxygen concentration and the sensor output current can vary unpredictably, reducing sensor accuracy.

The electrocatalytic effect of commonly used platinum sensor electrodes are known to deteriorate with time, with application of high current and high voltage, and with operation at high temperature. Current limiting properties of conventional electrochemical polarographic sensors can degrade due to thermal shock, gas erosion, and impurity deposition on the sensor.

Oxygen concentration sensing is required as an input in many conventional control systems, such as automotive internal combustion engine air/fuel ratio control. Further, such information is useful in diagnostic applications, such as for diagnosing oxygen storage and release capacity of conventional catalytic treatment devices. The performance of such control and diagnostics over time requires accurate oxygen sensing. In the event the oxygen sensor cannot be maintained in the current limiting range of operation, and therefore cannot provide an output current indicating oxygen concentration, it would be desirable that such condition be diagnosed so that corrective action may be taken to preserve control and diagnostics functions dependent thereon.

SUMMARY OF THE INVENTION

The present invention provides for operation of an electrochemical polarographic sensor with a diagnosis function to indicate sensor operation out of the current limiting range of operation.

More specifically, the present invention drives a wide range electrochemical polarographic oxygen sensor under a drive voltage designed to maintain the sensor in the current limiting range of operation. Small perturbations in the drive voltage are applied at a level to cause a measurable variation in the sensor output current. The perturbations are sufficiently small so as to not drive the sensor out of the current limiting range of operation. The perturbations should not pass through as variations in the sensor output for a healthy sensor operating in the current limiting range. As such, any variation in the sensor output signal corresponding to the drive signal perturbations are diagnosed as indicating operation outside the voltage limiting range. An indication of such faulty operation is made to effect sensor repair or replacement. The perturbations may be provided in the form of a low amplitude alternating current ingredient in the sensor drive signal substantially at a fixed frequency. The sensor output current may be inspected for any significant signal content at the fixed frequency, such as through a signal demodulation process. A fault condition characterized by the sensor operating outside the current limiting range of operation in which sensor output current indicates the concentration of oxygen in the engine exhaust gas is diagnosed when a significant signal content is detected at the fixed frequency.

BRIEF DESCRIPTION OF THE DRAWINGS

The invention may be best understood by reference to the preferred embodiment and to the drawings in which.

DESCRIPTION OF THE PREFERRED EMBODIMENT

Figure 1:
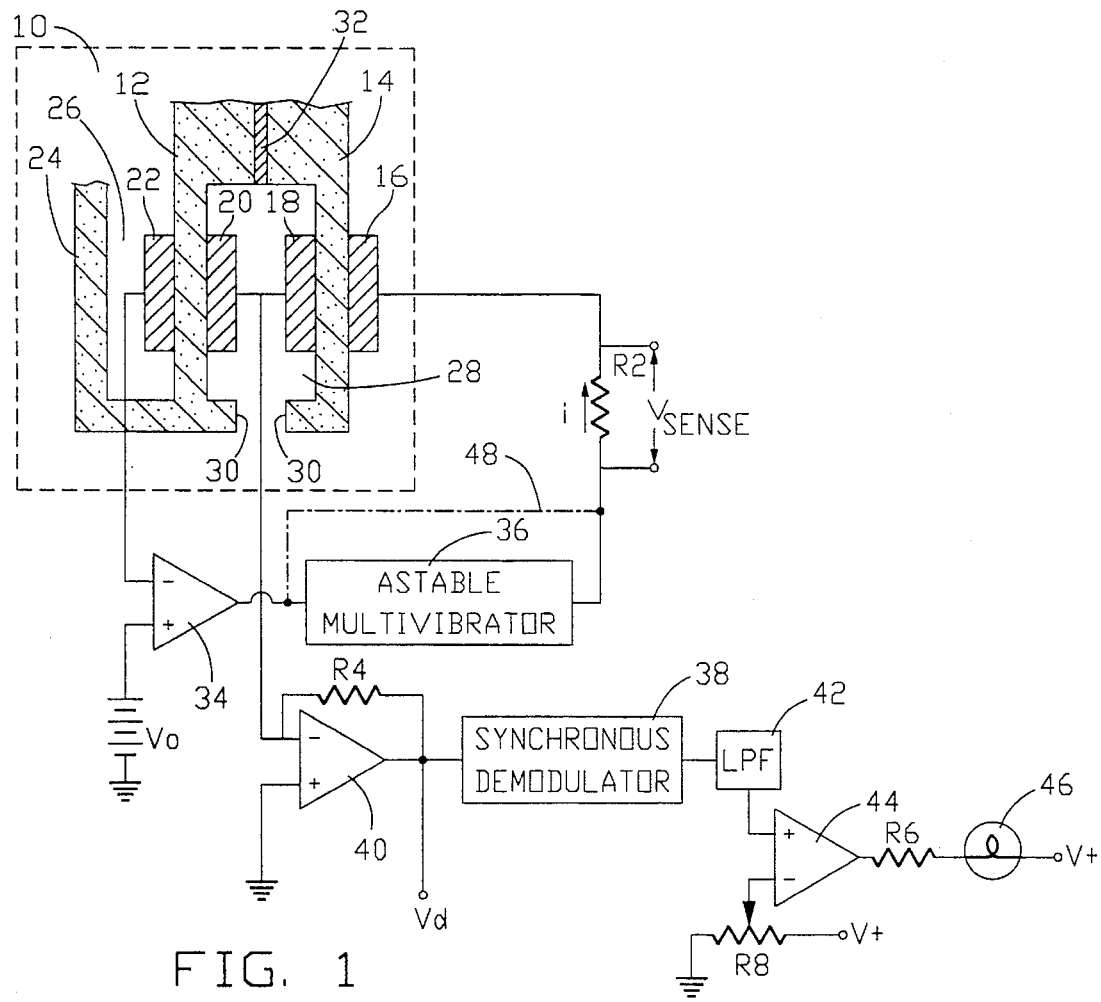
FIG. 1 is a schematic description of the oxygen sensor and diagnostic hardware of the preferred embodiment.

Referring to FIG. 1, electrochemical polarographic-based oxygen sensor 10 includes a pump cell having electrodes 16 and 18 between which is disposed solid electrolyte material 14, such as doped zirconia, and a sensing cell, such as a conventional Nernst cell including air reference electrode 22 exposed to air reference, such as ambient air in region 26, and sensing electrode 20 between which is disposed a solid electrolyte material 12, such as doped zirconia. Solid electrolytes 12 and 14 are isolated from each other by insulator 32 to minimize cross talk between the cells and to increase sensor signal to noise ratio. The sensing cell can be made of any known solid oxide electrolyte such as ceria, thoria, or zirconia in which proper alio-valent dopants are added to maintain a proper level of oxide mobility at elevated temperatures. Examples of acceptable dopants are Ca, Bi, La, Mg, Sc, Y, and Gd.

Electrodes can be any metal, metal alloy, ceramic, or metal-ceramic composite material, as long as such material has proper electrical conductivity including mixed ionic-electronic conductivity, and proper electrochemical catalytic properties. Examples of such electrode materials are Pt, Pt—Pd alloy, PT—Rh alloy, Ag, Ag alloy, Au, Au alloy, $LaMnO_3$, and $LaCrO_3$ ceramics with proper dopants such as alkaline earth elements. Insulator 32 can be made of alumina or composite of alumina and doped zirconia or may be other composite materials having similar thermal-mechanical properties as those of solid electrolyte materials.

The sensor 10 may be fabricated through such generally known methods as ceramic forming methods such as cold press or extrusion methods. Additionally, thick film methods may be used, such as tape casting, plasma spray, screen print or dipping. Still further, thin film methods may be used, including CVD, PVD, MOCVD, MOD, or Sol-Jet methods, as are generally known in the art.

Electrodes 18 and 20 share a common gas chamber 28 into which is provided a representative flow of test gas, such as internal combustion engine exhaust gas for sensing of the oxygen concentration thereof. The gas chamber 28 has a gas diffusion limiting means 30, such as an aperture to limit the gas flux into and out of the chamber 28. The gas diffusion limiting means may be holes put in the electrolyte membranes before or after the sensing element has been sintered. The methods of hole making include conventional saw cutting, drilling, laser drilling, and die-punching. Semipermeable structure of materials may also be used, including ceramics, metals, or composite. They can be stand-alone structure without other function, or can be semipermeable structure which also functions as a sensor electrode, electrolyte, or protection layer of the electrode.

A potential across the electrodes 16 and 18 of the pump operates to drive the pump cell to pump oxygen into and out of the gas chamber 28. The pumping action operates to establish an electromotive force EMF across the electrodes 20 and 22 of the sensing cell, which EMF is provided through a feedback circuit for driving the pump cell.

By maintaining the EMF across the electrodes 20 and 22 within a predetermined voltage range corresponding to a current limiting range of operation of the sensor, the pump current is maintained at a level at which is linearly proportional to the oxygen flux into and out of the gas chamber 28. Sensor output current i passing from across the electrolyte 14 of the pump cell indicates the oxygen flux and is provided as a sensor output signal for engine control and diagnostics, such as feedback signal for closed-loop engine air/fuel ratio control, or a sense signal for diagnosing oxygen storage and release activity of a catalytic converter or other engine exhaust gas catalytic treatment means, as is generally understood in the art.

Figure 2:
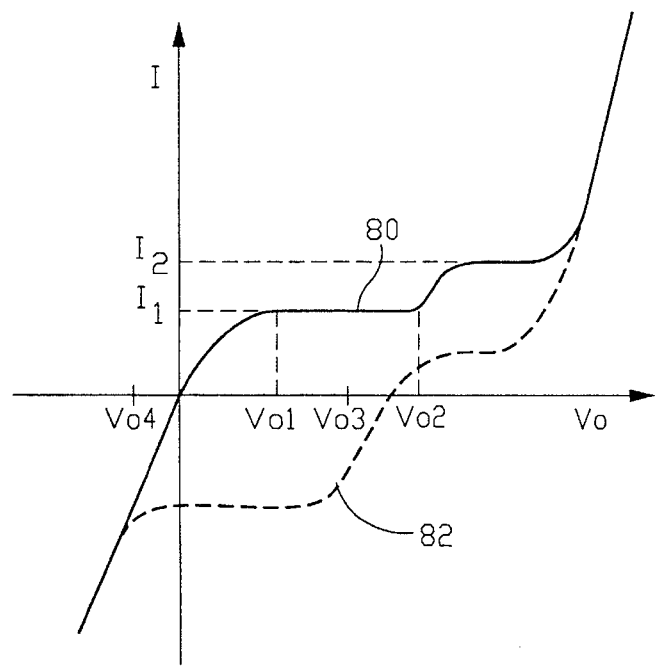
FIG. 2 is a graphical description of the relationship between a control voltage input and an output current of the oxygen sensor of FIG. 1.

The voltage Vo applied to the sensor 10 of FIG. 1 is established at a level designed to maintain the sensor in the current limiting range of operation. FIG. 2 illustrates the current-voltage characteristics of the sensor 10 for a given oxygen concentration in the test gas. Solid curve 80 of FIG. 2 represents the characteristics for lean test gas having an abundance of oxygen, and broken curve 82 represents the characteristics for rich test gas having a deficiency of oxygen. With lean gas in the chamber 28 of FIG. 1, a positive Vo provides for pumping of oxygen out of chamber 28 of FIG. 1 with the supply of oxygen limited by the aperture 30.

At a small Vo, such as a Vo less than Vo1 of FIG. 2, there is an ample supply of oxygen and the current i of FIG. 2 is controlled by the electrode polarization of the pump cell, illustrated as the current less than I1. The relationship between the current and voltage of FIG. 2 is non-linear in this range of operation. For Vo values greater than Vo1 and less than Vo2, the supply of oxygen becomes limited by the aperture 30 of FIG. 1 and the oxygen flux reaches its limiting value. An increase of Vo will not change the value of pumping current in this range of operation and the pumping current reaches a plateau (substantially at current I1 in FIG. 2). This limiting current I1 represents the maximum flow of current that can be supported by the oxygen concentration in the test gas, such as the engine exhaust gas.

Further increasing Vo beyond Vo2 can provide for a stripping of oxygen from gas species such as $CO_2$ and $H_2O$, and the current will rise again. Such rise in current is not related to the oxygen concentration in the test gas and can lead to inaccuracy in the transduced oxygen content of the test gas. The current will continue to rise with Vo greater than Vo2 until the supply of $Co_2$ and $H_2O$ is again limited by the aperture 30 of FIG. 1. At such point, the current will reach yet another plateau in the current-voltage plot (substantially at current I2). The limiting current I2 represents the maximum oxygen flux that can be supplied by the $O_2$, $CO_2$, and $H_2O$ concentrations in the exhaust.

If Vo is increased further, oxygen can be stripped from the solid electrolyte 14 of FIG. 1 and electron current begins to be directly injected into the solid electrolyte, resulting in a highly nonlinear current-voltage relationship. Such range of operation can severely reduce the accuracy of the sensor 10 of FIG. 1. For Vo less than zero, oxygen is pumped back into chamber 28 of FIG. 1. Since there is no gas restricting means like aperture 30 constraining such pumping action, the pump current corresponding to the negative voltage Vo will be highly non-linear.

For rich test gas characterized by a deficiency of oxygen, a similar current-voltage characteristic is obtained except the entire curve is shifted, as illustrated by the broken curve 82 of FIG. 2 which is shifted downward in current magnitude from the lean characteristic 80. The shift is due to the spontaneous EMF of the sensing cell. For extremely small Vo, such as Vo less than the spontaneous EMF of the sensing cell, pumping current becomes negative and oxygen is pumped back into the gas chamber 28 of FIG. 1. The pumped oxygen will be consumed on the surface of electrode 18 in accordance with generally known electrocatalytic oxidizing effects.

Initially under such operation, there may be an abundance of fuel and the current is controlled by the electrode polarization and is non-linear. Since the supply of fuel gas is limited by the aperture 30, at higher oxygen pumping rates, the supply of fuel is rapidly depleted and reaches a limiting value. A current limiting range is therefore present for voltages between Vo3 and Vo4 within which current remains substantially constant for changing Vo. The limiting current in this range of operation represents the concentration of fuel in the test gas.

If Vo is decreased below Vo4, the oxygen can be directly pumped into gas chamber 30 of FIG. 1 without the above-described fuel gas constraints, resulting in a non-linear current-voltage relationship not indicating oxygen concentration in the exhaust gas. If Vo is increased to a value greater than Vo3, oxygen will again be stripped away from $CO_2$ and $H_2O$, as well as the solid electrolyte 14 of FIG. 1 and pumped out of chamber 28. The current will rise rapidly and potentially non-linearly as described in the lean case. Such current is not indicative of fuel concentration in the test gas.

Accordingly, accurate oxygen concentration information is made available through the sensor 10 of FIG. 1 by monitoring pumping current i, such as by measuring the voltage drop Vsense across a sense resistor R2 while the sensor 10 is maintained in a current limiting range of operation. Such range of operation may be provided for by calibrating the proper Vo to be applied to the sensor via op-amp driver 34. Specifically, air reference electrode 22 is electrically connected to the inverting terminal of op-amp driver 34, the non-inverting terminal of which is connected to a fixed amplitude voltage source Vo, calibrated to a substantially fixed amplitude. Broken line 48 represents that an electrical connection may be provided from the driver 34 output through the series resistor R2 to the pump cell electrode 16 for driving the pump cell in a closed loop sensor configuration. As long as the drive voltage Vo maintains the sensor in the current limiting range of operation, illustrated in FIG. 2 as the range of operation between voltages Vo1 and Vo2 for lean test gas and between voltages Vo3 and Vo4 for rich test gas, the voltage drop Vsense indicates oxygen concentration in the test gas.

Figure 3:
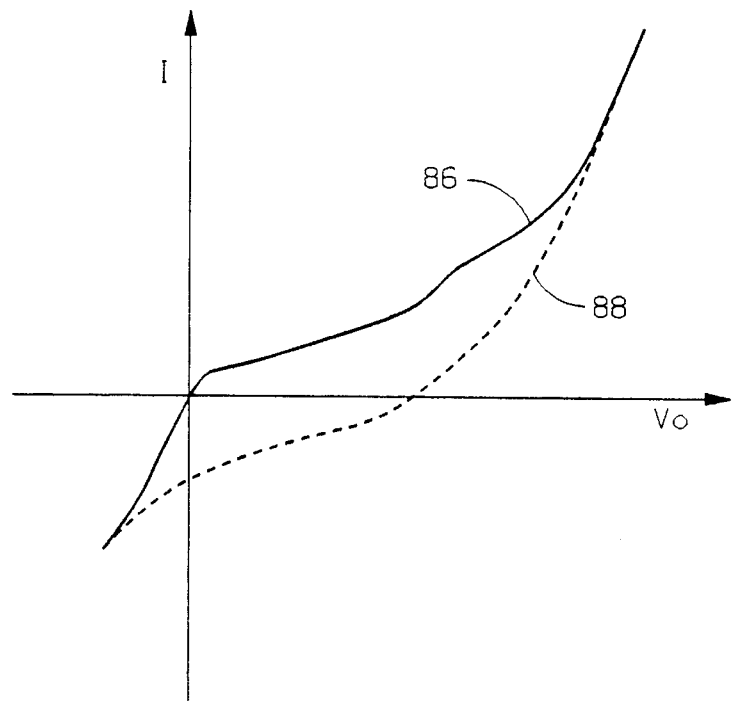
FIG. 3 is a graphical description of the relationship of FIG. 2 for an oxygen sensor having deteriorated current limiting properties.

Certain fault conditions including deterioration in the electrocatalytic effect of the sensor electrodes 16–22 of FIG. 1 and deterioration in the gas limiting means of the sensor 10 of FIG. 1 may result in operation outside of a current limiting range of operation even when Vo is properly set. For example, FIG. 3 illustrates the current-voltage characteristic for a typical electrochemical polarographic sensor, such as sensor 10 of FIG. 1 having deterioration in the electrocatalytic effect of the sensor electrodes, such as due to sensor aging, sensor exposure to extreme voltage, current, or temperature, or sensor exposure to impurities. Curve 86 of FIG. 3 illustrates the characteristic for lean test gas and curve 88 for rich test gas, both of which are characterized by a non-linear current-voltage relationship, providing for no current limiting range of operation.

Figure 4:
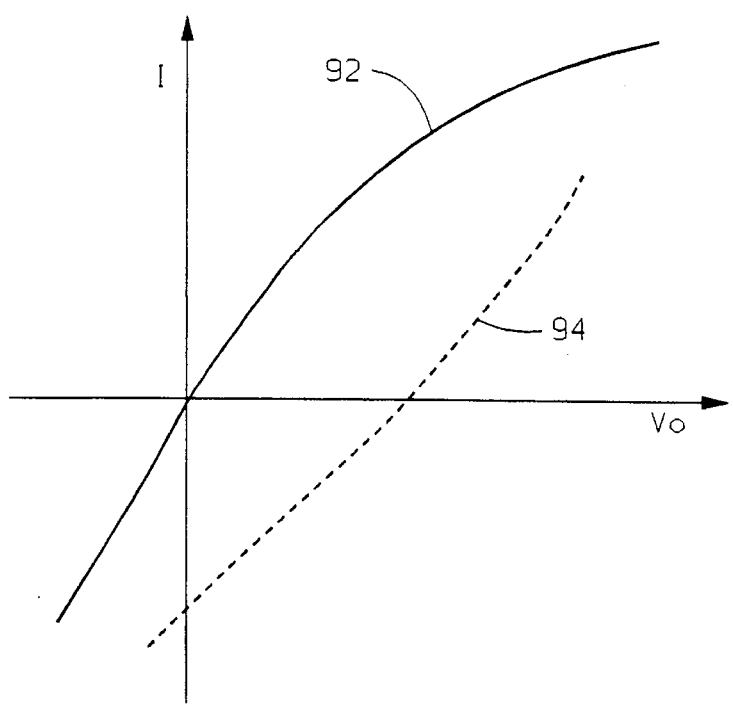
FIG. 4 is a graphical description of the relationship of FIG. 2 for an oxygen sensor having deteriorated electrocatalytic effects on the sensor electrodes.

FIG. 4 illustrates the current-voltage characteristic for a typical electrochemical polarographic sensor, such as sensor 10 of FIG. 1, having deterioration in the gas limiting means due, for example, to thermal shock, gas erosion, and impurity deposition on the sensor. Curve 92 of FIG. 4 illustrates the characteristic for lean test gas and curve 94 for rich test gas, both of which are characterized by a non-linear current-voltage relationship, providing for no current limiting range of operation. Under such conditions as illustrated in FIGS. 3 and 4, open loop control of sensor drive voltage at or near a calibrated voltage Vo may not provide for accurate oxygen concentration indication through analysis of pumping current i of FIG. 1.

To indicate when such fault conditions as illustrated in the FIGS. 3 and 4 are present, the circuitry of FIG. 1 is provided. A conventional astable multivibrator 36 or other fixed frequency generator means is provided between the output of driver 34 and sense resistor R2, and being driven when driver 34 is operating to drive pump cell including electrodes 16 and 18. A first output of astable multivibrator 36 is provided to electrode 16 through series sense resistor R2, and a second output is provided as a reference input to conventional synchronous demodulator 38.

Figure 5:
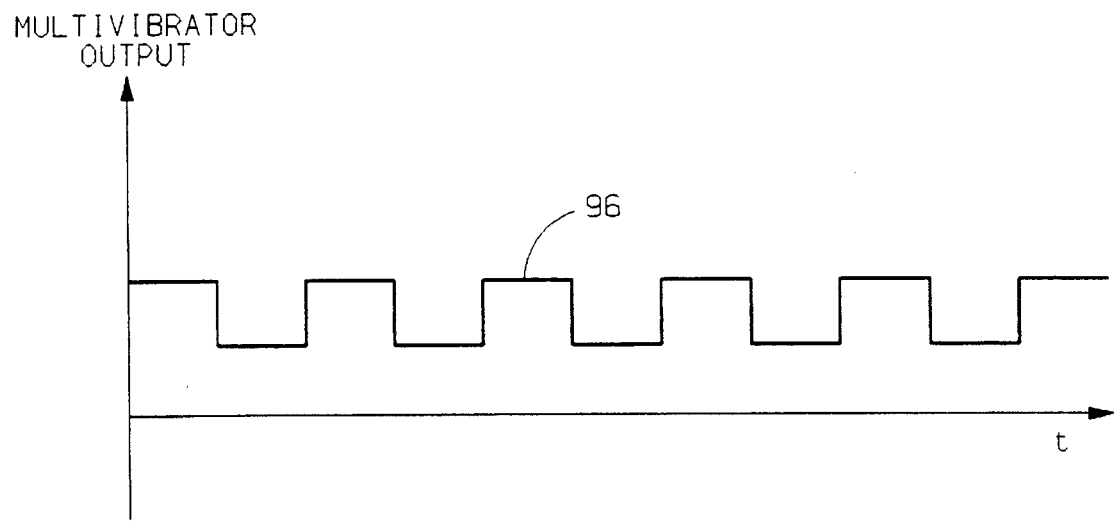
FIG. 5 is a graphical description of the output signal of a multivibrator stage of the hardware of FIG. 1.

The fixed frequency output signal provided by the multivibrator 36 is illustrated by signal 96 of FIG. 5, in accord with commercially available multivibrator output signals. The voltage at electrodes 18 and 20 is provided to inverting input of common op-amp 40 configured as a conventional current to voltage converter to convert the sensor pump current to a voltage signal available as a sensor output voltage indicating oxygen concentration and available as a diagnostic output signal in accord with this invention. Non-inverting input of current to voltage converter 40 is provided at ground reference. Op-amp 40 output is applied as a data input to synchronous demodulator 38, for demodulation at the frequency of the reference signal output by astable multivibrator 36. The op-amp 40 output may also be provided as a sense and diagnostic output voltage Vd, to be described.

The output of synchronous demodulator 38 is provided, in but one diagnostic approach in accord with this invention, to a conventional low pass filter circuit 42, the output of which is applied to the non-inverting input of common op-amp 44 provided in a voltage comparator configuration. The inverting input of op-amp 44 receives a voltage reference signal provided by voltage supply signal V+ divided down to a desired reference level through a setting of conventional potentiometer R8. Op-amp 44 output is connected, through series resistor R6 to indicator 46, such as a conventional lamp or LED, the opposing terminal of which is connected to a supply voltage V+.

Functionally, application of predetermined voltage Vo to driver op-amp 34 initiates operation of astable multivibrator 36 to provide an output signal through series resistor R2 to pump cell electrode 16 to establish a potential across pump cell to pump oxygen into or out of gas chamber 28, as described. Curve 96 of FIG. 5 illustrates a typical output signal of the multivibrator 36. The voltage amplitude Vp of the pulses of signal 96 are maintained relatively low, such as less than or equal to 0.5 volts, so as to provide an a.c. ingredient in the pump cell drive signal of substantially known frequency. The frequency of signal 96 must be maintained below the frequency at which the electrode double layer capacitance will be electrically shorted. If the voltage Vo is properly calibrated and set and if the sensor is "healthy", the sensor will operate in the current limiting range.

Current limiting operation ensures that the sensor output current will be insensitive to and carry substantially no a.c. component at the frequency of the multivibrator output signal, such as signal 96 of FIG. 5, as the pumping current of the sensor in such range of operation is substantially insensitive to change in applied voltage, and since the amplitude Vp (FIG. 5) of the a.c. component of signal 96 is sufficiently small to not drive the sensor out of the current limiting range of operation. Accordingly, there will be substantially no a.c. component at the frequency of signal 96 of FIG. 5 in the output signal Vd as illustrated by signal 100 of FIG. 6.

Figure 6:
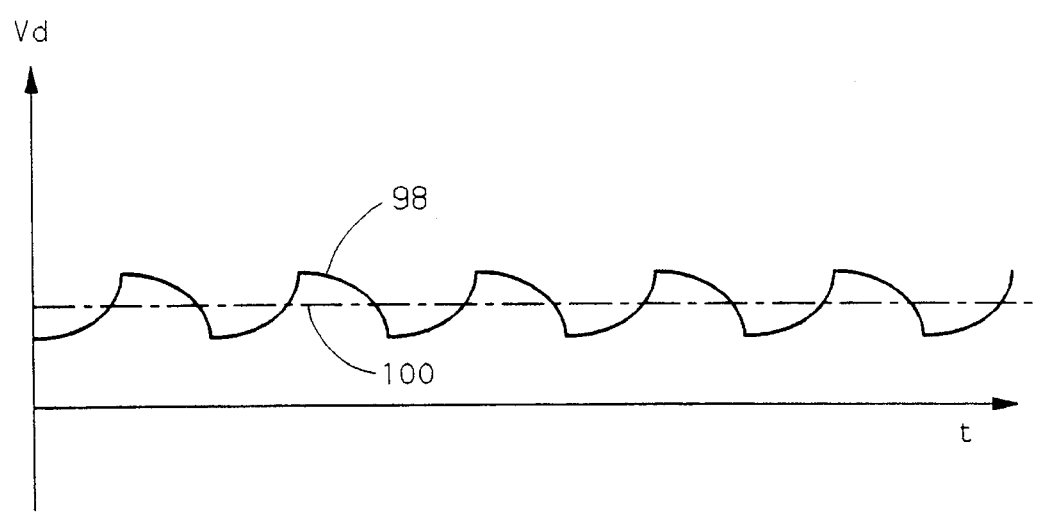
FIG. 6 is a graphical description of the output signal of the diagnostic hardware of FIG. 1 for faulty and fault-free oxygen sensors.

By monitoring output signal Vd for such an a.c. component at the frequency of signal 96 of FIG. 5, current limiting operation may be diagnosed. For example, FIGS. 3 and 4 illustrate that for rich or lean test gasses, sensor current is sensitive to voltage fluctuations, to the extent that the a.c.

component of the sensor drive voltage, such as characterized by signal 96 of FIG. 5, will be manifest in the pumping current of the sensor, and may be detected by monitoring signal Vd. Signal 98 of FIG. 6 illustrates the sensor output signal Vd under such faulty sensors, such as sensors having the current-voltage characteristic illustrated in FIGS. 3 and 4. The described sensor fault conditions, and indeed any other fault conditions of the sensor that may deteriorate its current limiting properties may be diagnosed and indicated in this manner. It should be noted that signal Vd may be used as the sensor output voltage for transducing oxygen concentration of the test gas, as the pumping current i from electrode 16 to electrode 18 is the current input to current to voltage converter 40, which is substantially the same as current i across sense resistor R2 of FIG. 1. Additionally, it should be noted that, in an alternative embodiment of this invention, the signal Vsense may be monitored for diagnosing sensor 10 operation with conventional a.c. signal detection circuitry, wherein any a.c. component detected in the signal Vsense or in the current i of FIG. 1 substantially at the frequency of the multivibrator output signal may indicate a sensor fault condition characterized by the sensor operating outside the current limiting range, in accord with this invention.

In further detail, FIG. 6 illustrates output signal Vd of the circuit of FIG. 1 for two cases. In a first case, the sensor output signal Vd taken from the node formed between the pump cell and the sensing cell of the sensor as illustrated in FIG. 1, takes the form of signal 100 for a sensor operating in its current limiting range of operation, in which the a.c. component of drive signal 96 (FIG. 5) results in substantially no a.c. component in Vd at the frequency of signal 98. The sensor does not respond to the a.c. voltage fluctuations in the drive signal, indicating the current limiting behavior expected in the range of operating of the sensor 10 in which sensor output current corresponds to the oxygen concentration in the test gas, as described.

In a second case, the sensor output signal Vd taken from the node formed between the pump cell and the sensing cell of the sensor as illustrated in FIG. 1 takes the form of signal 98 for a sensor not operating properly in its current limiting range of operation, for example due to a sensor fault condition, wherein the sensor output current may not accurately indicate oxygen concentration in the test gas, which may reduce the performance of control and diagnostics systems requiring oxygen concentration information from the sensor. Signal 98 includes an a.c. component that substantially matches the frequency of the sensor drive voltage signal, such as signal 96 of FIG. 5. Diagnosis of a sensor not operating in its current limiting range may then, in this embodiment, simply require detection of an a.c. component in the signal Vd of FIG. 1 having a frequency substantially matching the frequency of the a.c. component of the sensor drive signal. As described, such detection may also be applied to signal Vsense or to the equivalent current signal i, including any current signal substantially indicating the pumping current across electrodes 16 and 18 of FIG. 1.

To provide for such detection in this embodiment, detection circuitry is included in FIG. 1 along with the described sensor drive circuitry, including the current to voltage converter 40 having the input voltage Vd being passed to the data input of the synchronous demodulator 38. The demodulator 38 will demodulate current to voltage converter output signal at the frequency of the reference input to the demodulator by the multivibrator 36, and pass the output signal magnitude to low pass filter 42 at a high voltage level when a substantial frequency match occurs between the data and reference inputs, in accord with conventional understanding in the art.

A high demodulator output signal will pass, following a short filter delay, through the low pass filter 42 for comparison with the reference voltage applied to the inverting input of voltage comparator op-amp 44. If the demodulator output voltage exceeds the reference voltage, the comparator will be driven to a low output impedance operation mode, providing for a sinking of current from the voltage source V+through the indicator 46 to the op-amp 44 output stage. Such current will energize the indicator 46, such as by illuminating a light, turning on an LED, etc. to indicate a sensor fault condition. If the demodulator output signal is less than the reference voltage applied to the inverting input of the comparator 44, the comparator output will remain in a high impedance operation mode, preventing current from passing through the indicator 46, and no fault condition will be indicated.

The low pass filter 42, which may take the form of other conventional filter means generally understood in the art, is provided to attenuate transient high output signals from demodulator 38, such as output signals that may occur during brief demodulation periods, such as due to noise or other signal or system disturbances. Such transients, event if caused by a very short period of sensor operation outside of the current limiting range, may be blocked by the filter so that no indication of a fault condition is provided. Such may be desired in one embodiment of this invention to only allow for an indication of a sensor fault condition when a sustained period of sensor operation outside the current limiting range occurs, such as may begin to reduce control or diagnostic accuracy.

The reference voltage applied to the inverting input of comparator 44 decreases sensitivity of the diagnostic circuitry of FIG. 1 to noise and other disturbances which may operate to cause the non-inverting comparator input to exceed the inverting input. Only when the non-inverting input reaches a significant voltage magnitude will the comparator turn on, providing for energization of the indicator 46, to provide a reliable, robust diagnostic in accord with this embodiment.

The indicator 46 may take the form of a lamp, light emitting diode or other visual indication means generally known in the art, or may easily be conditioned to appear as an input to a controller (not shown), so that the controller, through a periodic polling of the input or through an interrupt caused by a change in state of the input, may comprehend the health of the sensor.

Other diagnostic operations may be provided through the exercise of ordinary skill in the art to diagnose sensor operation by analyzing the signal Vd of FIG. 1. By monitoring the signal Vd or the pumping current for an a.c. component having a frequency that corresponds to the frequency of the a.c. component of the sensor drive signal, and by diagnosing sensor operation outside the current limiting range when such an a.c. component is detected, the diagnostic of this embodiment is provided for in accord with this invention.

A number of circuitry variations may be provided over the circuitry illustrated in FIG. 1 to carry out such diagnostic. One such variation provides that the astable multivibrator 36 may be placed between the voltage source Vo and the non-inverting input of comparator 34, to be energized by input signal Vo and to provide an output signal including an a.c. component to the non-inverting input of comparator 34, so that the drive voltage of the pump cell of FIG. 1 includes an a.c. component to diagnose current limiting operation, as described. In such alternative embodiment, the astable multivibrator 36 is omitted from the node between the op amp 34 output and the sense resistor R2, but still must provide a reference input to synchronous demodulator 38, as in the case of the described preferred embodiment.

The preferred and alternative embodiments for the purpose of explaining this invention is not to be taken as limiting or restricting this invention since many modifications may be made though the exercise of ordinary skill in the art without departing from the scope of this invention.

The embodiments of the invention in which a property or privilege is claimed are described as follows:

1. A diagnostic apparatus for indicating current limiting behavior of an exhaust gas sensor having a gas chamber with a gas diffusion limiting means and a pump cell exposed to the gas chamber for pumping oxygen into and out of the gas chamber, creating a sensor electromotive force which is applied to drive circuitry for providing an electrical drive signal applied to the pump cell for driving the pump cell, comprising:

circuitry for applying a signal perturbation to the electrical drive signal;

sense circuitry for sensing change in electrical current through the sensor resulting from the applied signal perturbation; and an indicator for indicating the sensed change in electrical current to indicate current limiting behavior of the sensor.

2. The apparatus of claim 1, wherein the signal perturbation is an alternating current perturbation means providing for an alternating current component in the drive signal.

3. The apparatus of claim 1, wherein the sensor further comprises a sensing cell exposed to the gas chamber for sensing the sensor electromotive force, wherein the sensing cell is electrically coupled to the drive circuitry for communicating the sensor electromotive force thereto.

4. The apparatus of claim 3, wherein the sensing cell comprises a Nernst cell.

5. The apparatus of claim 1, wherein the circuitry for applying a signal perturbation to the electrical drive signal comprises a signal generator for generating an output signal that varies in magnitude substantially at a frequency, and wherein the sense circuitry further comprises demodulation circuitry for demodulating the electrical current through the sensor substantially at the frequency to determine the strength of the signal content substantially at the frequency.

6. A method for diagnosing operating performance of an internal combustion engine exhaust gas sensor having a gas chamber with a gas diffusion limiting means and a pump cell driven to create a sensor electromotive force by pumping oxygen into and out of the gas chamber through the gas diffusion limiting means, the sensor electromotive force being applied to a pump cell driver for generating and applying to the pump cell an electrical drive signal for driving the pump cell, wherein electrical current through the pump cell indicates the flux of oxygen into and out of the gas chamber to indicate oxygen concentration in the exhaust gas when the sensor is operating in a current limiting state, the method comprising the steps of:

varying the electrical drive signal in accord with a signal variation;

monitoring the electrical current through the pump cell to detect any change in electrical current corresponding to the signal variation; and diagnosing a sensor fault condition characterized by the sensor not operating in the current limiting state when a change in electrical current corresponding to the signal variation is detected.

7. The method of claim 6, wherein the internal combustion engine exhaust gas sensor includes a Nernst cell exposed to the gas chamber for sensing the sensor electromotive force.

8. The method of claim 6, wherein the varying step varies the drive signal substantially at a frequency of variation, and wherein the monitoring step monitors the electrical current through the pump cell to detect any electrical current component substantially at the frequency of variation.

9. The method of claim 6, wherein the varying step further comprises the steps of:

generating an alternating current waveform having a frequency;

combining the alternating current waveform with the electrical drive signal to vary the electrical drive signal; and applying the varied electrical drive signal to the pump cell for driving the pump cell.

10. The method of claim 9, wherein the monitoring step further comprises the steps of:

demodulating the sensor electrical current substantially at the frequency to provide a diagnostic signal indicating the signal content of the electrical current substantially at the frequency;

providing a reference signal of signal magnitude;

comparing the diagnostic signal with the reference signal;

and wherein the diagnosing step diagnoses the sensor fault condition when the diagnostic signal exceeds the reference signal.

11. The method of claim 10, wherein the monitoring step further comprises the step of:

reducing a rate of change of the diagnostic signal in accord with a time constant, and wherein the comparing step compares the diagnostic signal having a reduced rate of change to the reference signal to protect against misdiagnosis of a sensor fault condition.

12. The method of claim 11, wherein the reducing step reduces the rate of change of the diagnostic signal by lag filtering the diagnostic signal by a lag filter process having a filter constant corresponding to the time constant.

* * * * *